(12) United States Patent
Elias

(10) Patent No.: US 6,599,694 B2
(45) Date of Patent: Jul. 29, 2003

(54) METHOD OF CHARACTERIZING POTENTIAL THERAPEUTICS BY DETERMINING CELL-CELL INTERACTIONS

(75) Inventor: Kathleen A. Elias, San Francisco, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 09/741,721

(22) Filed: Dec. 18, 2000

(65) Prior Publication Data

US 2002/0160442 A1 Oct. 31, 2002

(51) Int. Cl.$^7$ .................. C12Q 1/00; G01N 33/574; G01N 1/30

(52) U.S. Cl. .................. 435/4; 435/7.23; 435/40.51

(58) Field of Search .................. 435/4, 7.23, 40.51

(56) References Cited

U.S. PATENT DOCUMENTS

| | | |
|---|---|---|
| 4,818,710 A | 4/1989 | Sutherland et al. |
| 4,922,092 A | 5/1990 | Rushbrooke et al. |
| 4,959,301 A | 9/1990 | Weaver et al. |
| 4,965,725 A | 10/1990 | Rutenberg |
| RE34,214 E | 4/1993 | Carlsson et al. |
| 5,287,272 A | 2/1994 | Rutenberg et al. |
| 5,355,215 A | 10/1994 | Schroeder et al. |
| 5,526,258 A | 6/1996 | Bacus |
| 5,548,661 A | 8/1996 | Price et al. |
| 5,655,028 A | 8/1997 | Soll |
| 5,733,721 A | 3/1998 | Hemstreet, III et al. |
| 5,741,648 A | 4/1998 | Hemstreet et al. |
| 5,776,748 A | 7/1998 | Singhvi et al. |
| 5,790,692 A | 8/1998 | Price et al. |
| 5,790,710 A | 8/1998 | Price et al. |
| 5,804,436 A | 9/1998 | Okun et al. |
| 5,856,665 A | 1/1999 | Price et al. |
| 5,893,095 A | 4/1999 | Jain et al. |
| 5,919,646 A | 7/1999 | Okun et al. |
| 5,932,872 A | 8/1999 | Price |
| 5,962,250 A | 10/1999 | Gavin et al. |
| 5,962,520 A | 10/1999 | Smith et al. |
| 5,976,825 A | 11/1999 | Hochman |
| 5,989,835 A | 11/1999 | Dunlay et al. |
| 5,991,028 A | 11/1999 | Cabib et al. |
| 5,995,143 A | 11/1999 | Price et al. |
| 6,007,996 A | 12/1999 | McNamara |
| 6,008,010 A | 12/1999 | Greenberger et al. |
| 6,083,763 A | 7/2000 | Balch |
| 6,103,479 A | 8/2000 | Taylor |
| 6,146,830 A | 11/2000 | Friend et al. |
| 6,222,093 B1 | 4/2001 | Marton et al. |
| 6,345,115 B1 | 2/2002 | Ramm et al. |

FOREIGN PATENT DOCUMENTS

| | | |
|---|---|---|
| EP | 0317139 | 5/1989 |
| EP | 0468 705 A2 | 7/1991 |
| EP | 0902394 A1 | 3/1999 |
| WO | WO 87/02802 | 5/1987 |
| WO | WO 94/11841 | 5/1994 |
| WO | WO 95/10036 | 4/1995 |
| WO | WO 9522749 | 8/1995 |
| WO | WO 98/05959 | 2/1998 |
| WO | WO 98/38490 | 9/1998 |
| WO | WO 98/44333 | 10/1998 |
| WO | WO 99/08091 | 2/1999 |
| WO | WO 99/17116 | 5/1999 |
| WO | WO 99/39184 | 8/1999 |
| WO | WO 99/44062 | 9/1999 |
| WO | WO 00/03246 | 1/2000 |
| WO | WO 00/17624 | 3/2000 |
| WO | WO 00/17643 | 3/2000 |
| WO | WO 00/17808 | 3/2000 |
| WO | WO 00/26408 | 5/2000 |
| WO | WO 00/31534 | 6/2000 |
| WO | WO 00/33250 | 6/2000 |
| WO | WO 00/49540 | 8/2000 |
| WO | WO 00/60356 | 10/2000 |

OTHER PUBLICATIONS

Hofland et al, Role of Tumor–Derived Fibroblasts in the Growth of Primary Cultures of Human Breast–Cancer Cells: Effects of Epidermal Growth Factor and the Somatostatin Analogue octreotide, 1995, Int. J. Cancer, 60, 93–99.*
Stearns et al, Interleukin 10 (IL–10) Inhibition of Primary human Prostate Cell–induced Angiogenesis: IL–10 Stimulation of Tissue Inhibitor of Metalloproteinase–1 and Inhibition of Matrix Metalloproteinase (MMp)–2/MMP–9 Secretion, Jan. 1999, . . . Con't . . . .*
Clinical Cancer Research, vol. 5, pp. 189–196.*
Printed from Website on Apr. 12, 2000, http://www.automatedcell.com, 9 pages.
"An Integrated Method to Determine Epithelial Transport and Bioactivity of Oral Drug Candidates in Vitro," *Pharmaceutical Research*, vol. 13, No. 1, pp. 23–27, 1996.

(List continued on next page.)

Primary Examiner—John S. Brusca
(74) Attorney, Agent, or Firm—Lauren L. Stevens; Beyer Weaver & Thomas LLP

(57) ABSTRACT

A method quantitatively analyzes images of two different cell types that interact in producing and maintaining a disease state or other biological condition. The two separate cell types are exposed to an agent or stimulus suspected of influencing the biological condition (e.g., the agent might be a potential therapeutic for treating a cancer). The two different cell types are co-cultured or otherwise allowed to interact with one another before and during exposure to the agent. The images of the cells show how the agent affects the cells' phenotypes, including their viability, migration patterns, etc. The method generates a quantitative phenotype for each cell type by quantitatively analyzing the cell images via an automatic procedure. The quantitative phenotypes typically take the form of a group of scalar or vector descriptors that together provide a "fingerprint." The descriptors may be size values, positions, morphological values, intensity distributions, etc.

15 Claims, 8 Drawing Sheets

OTHER PUBLICATIONS

Uria JA, Stahle–Backdahl M, Seiki M, Fueyo A, Lopez–Otin C, "Regulation of Collagenase–3 Expression in Human Breast Carcinomas in Mediated by Stromal–Epithelial Cell Interactions", Cancer Res Nov. 1, 1997;57 (21):4882–8, Abstract.

Uria JA, Stahle–Backdahl M, Seiki M, Fueyo A, Lopez–Otin C, "Regulation of Collagenase–3 Expression in Human Breast Carcinomas in Mediated by Stromal–Epithelial Cell Interactions", Cancer Res Nov. 1, 1997;57 (21):4882–8, Abstract.

Rubas et al. "An Integrated Method to Determine Epithelial Transport and Bioactivity of Oral Drug Candidates in Vitro," *Pharmaceutical Research*, vol. 13, No. 1, pp. 23–27, 1996.

Sunblad et al., "The use of image analysis and automation for measuring mitotic index in apical confier meristems", © Oxford University Press 1998, Journal of Experimental Botany, vol. 49, No. 327, pp. 1749–1756.

* cited by examiner

METHOD OF CHARACTERIZING POTENTIAL THERAPEUTICS BY DETERMINING CELL-CELL INTERACTIONS

FIELD OF THE INVENTION

The systems and methods described herein provide for image capturing of living, dead, or fixed cells or cell fractions used to identify information about substances used on the cells or information about the cells themselves. Accordingly, the present invention can enable researchers and scientists to identify promising candidates in the search for new and better treatments and medicines, for example, in drug discovery and development. The principles enumerated herein may, with equal facility, be applied to other applications, including but not limited to use in environmental applications such as determining chemical toxicities and other non-pharmaceutical toxicology uses.

BACKGROUND OF THE INVENTION

Purified substances having a desirable combination bioactive properties are rare and often difficult to identify. Recent advances in traditional organic chemistry and the development of rapid combinatorial chemistry techniques have increased the number of compounds that researchers can test for a specific biological activity (e.g., binding to a target). Unfortunately, the vast majority of "hits" generated by such techniques do not possess the right combination of properties to qualify as therapeutic compounds. When these substances are subjected to low throughput cellular and animal tests to establish their therapeutic usefulness, they are typically found to fail in some regard. Unfortunately, such tests are time consuming and costly, thus limiting the number of substances that can be tested. In a like regard, the few hits that do possess the right combination of properties avoid recognition until after the throughput tests are conducted. With better early evaluation techniques, such promising candidates could be identified earlier in the development process and put on a fast track to the marketplace.

There have been some attempts to use image acquisition techniques to screen a large number of substances based upon biological cell information. One such attempt is described in International Application No. WO 98/38490 in the names of Dunlay, et al. Dunlay et al. generally describes a conventional image acquisition system. This conventional system collects and saves cellular images based on certain criteria that are predefined. Unfortunately, this system is has only a limited ability to predict a therapeutic usefulness of particular compounds or other agents.

One difficulty in predicting the clinical effectiveness of any agent is determining what concurrent effects it produces in normal cells, diseased versions of the normal cells, and other related cells. Diseases such as cancer often involve the interaction of various cell types such as cancerous epithelial cells and their stromal cells. During development of a potential new therapeutic, most research at the early stages focuses separately on the diseased cells or normal cells. To the extent that both cell types interact in producing or maintaining a disease state, there is no systematically rigorous technique for evaluating how a potential therapeutic affects their interaction.

What is needed therefore is a technique for quickly and quantitatively evaluating the affect of a potential therapeutic on a combination of various cell types that interact to produce or maintain a biological condition (e.g., cancer).

SUMMARY OF THE INVENTION

This need may be addressed by quantitatively analyzing images of two different cell types that interact in producing and/or maintaining a disease state or other biological condition. The two separate cell types are exposed to an agent or stimulus suspected of influencing the biological condition (e.g., the agent might be a potential therapeutic for treating a cancer). Typically, though not necessarily, the two different cell types are co-cultured or otherwise allowed to interact with one another before and during exposure to the agent. The images of the cells show how the agent separately affects each of the cell types. Specifically, the images show how the phenotype of each type changes (or does not change) upon exposure to the agent. In the context of this invention, the concept of a phenotype encompasses visual indicators showing viability, migration patterns, growth rates, extracellular matrix depositions, etc. The method generates quantitative phenotypes of the cells of cell types by quantitatively analyzing the cell images, usually via an automatic procedure. The quantitative phenotypes typically take the form of a group of scalar or vector descriptors that together provide a "fingerprint." The descriptors may be size values, positions, morphological values, intensity distributions, etc.

One aspect of the invention provides a method of evaluating the effect of interactions between distinct cell types. The method may be characterized by the following sequence: (a) providing a first cell culture of a first cell type and a second cell culture of a second cell type in a microenvironment; (b) imaging the first and second cell types after exposure to the agent; and (c) quantitatively evaluating one or more images obtained in (b) to identify any effects of the agent. To this end, the method employs quantitative representations of the phenotypes of the cells in the first and second cell cultures. This may show how the effects of the agent are mediated by interactions between the first and second cell cultures. The microenvironment mentioned above is typically a contained environment in which the cells of the first and second cell cultures share a common medium, thereby allowing the first and second cell types to interact in the common medium. In alternative embodiments, the cells of the distinct cell types are separately cultured and imaged. During the process, one of the cell types may be exposed to factors produced the other.

Frequently, a method of this invention includes separate operations of exposing the cells of the microenvironment to the agent and then imaging the first and second cell types. Thereafter, in determining how the agent affects quantitative representations of phenotypes of the cells, the system may be able to predict the effect of the agent in treating the biological condition of interest. The quantitative representation typically includes two or more scalar values or vectors that characterize morphological and/or compositional features of a cell.

The agents or stimuli considered for use with methods of this invention include a wide variety of perturbing influences, and, in some cases where the two cell types interact in particularly interesting ways, may even constitute the absence of a perturbation. Examples of agents contemplated for use with this invention will be discussed below. In many important applications, the agent is a biological material or chemical compound such as a drug candidate.

Many different biological conditions may be analyzed with the methods of this invention. Diseases are an important class of biological conditions. Specific examples of biological conditions that may be analyzed using this invention include cancers, Type I diabetes, Type II diabetes, neurodegenerative diseases, cardiovascular diseases, vascular disease, auto-immune diseases. In certain cases, the biological condition is normal unperturbed functioning of an organ or tissue and the agent causes one or more of the cell types to become abnormal.

The first and second cell types used with this invention are chosen to shed light on a particular biological condition. As mentioned, many of these cell types interact with one another to produce and/or maintain the biological condition. For example, where the biological condition is a cancer, the first cell type may be a cancerous epithelial cell type and the second cell type may be a mesenchymal (stromal) cell type, with both cell types taken from the same tissue or organ.

In one embodiment, the method involves applying the agent to both cancerous epithelial cells and either endothelial or stromal cells from the same tissue or organ. Then both cell types are imaged and the resulting images are evaluated to identify changes in at least one of the viability and the morphology of epithelial and endothelial or stromal cells. The changes of interest result from exposure to said agent. Finally, based upon any changes identified, predicting the agent's effect on the cancer.

Aspects of this invention also specify criteria for determining whether a particular agent will be "effective" in treating a particular biological condition. For example, when the biological condition is cancer, a potential therapeutic agent will be predicted to be effective when the images show that it has an EC50 for the cancerous epithelial cells that is substantially higher than the EC50 for the mesenchymal cells. Various other effects (beyond EC50) may be considered. These include changes in migration, extracellular matrix deposition, endocytosis, and cell shape.

Another aspect of the invention pertains to computer program products including a machine-readable media on which is stored program instructions for implementing a portion of or an entire method as described above. Any of the methods of this invention may be represented, in whole or in part, as program instructions that can be provided on such computer readable media.

These and other features and advantages of the present invention will be described below in more detail with reference to the associated drawings.

DETAILED DESCRIPTION OF THE INVENTION

Overview

Figure 1:
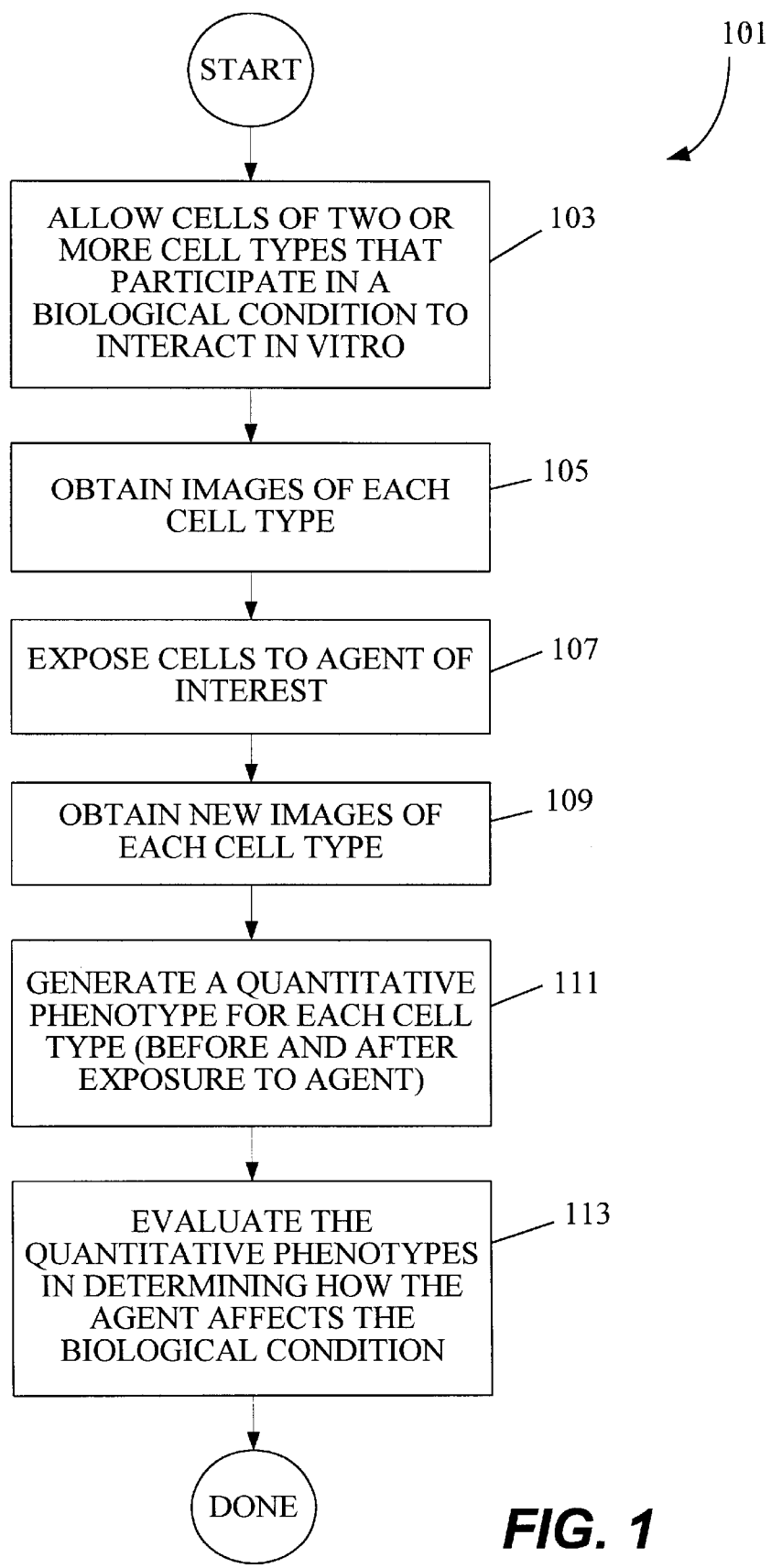
FIG. 1 is a process flow diagram depicting at a high level the important steps in an end-to-end process of this invention.

Generally, this invention relates to image analysis processes (methods) and apparatus allowing image analysis. But the image analysis is provided the context of a higher level process that involves developing experiments and research strategies for understanding certain biological conditions and developing agents for effectively alter these conditions. FIG. 1 presents a high-level process flow chart setting forth a sequence that might typically be followed in accordance with this invention.

As shown in FIG. 1, a research process 101 begins at 103 where two or more cell types are caused to interact with one another. Typically, these are cell types that are known to interact (or suspected to interact) in producing and/or maintaining the biological condition of interest. For example, cancerous epithelial cells and endothelial cells interact in some manner to facilitate vascularization (a biological condition) of tumors. Co-culturing the two or more cell types will allow them to interact. Other types of interaction conditions are possible.

After the cells have been allowed to interact for some period of time, they will be imaged (105). Typically, the imaging will involve capturing digital images of cells in a well or other culture medium. It may also involve some level of image processing, but for this example the sophisticated image processing will occur later at 111. After the cells have interacted for a period of time and have been imaged, they are treated with an agent (107). Numerous treatments are possible and will be discussed below. Following treatment with the agent, the cells are again imaged at 109. Depending upon the type of treatment, the cells may be imaged multiple times to understand how their phenotypes change over time. In some cases, the amount or level of the agent will be increased or decreased over time. In such cases, the process may capture separate images after each change in exposure to the agent.

With multiple images now available, the process generates a "quantitative phenotype" for each cell or each population of cells. For example, an image analysis system may generate one quantitative phenotype for the cell type A prior to exposure to the agent, another quantitative phenotype for cell type A after exposure to a first concentration of the agent, and yet another quantitative phenotype for cell type A after exposure to a second concentration of the agent. The system may generate a similar sequence of quantitative phenotypes for cell type B at the various stages of treatment. The concept of a "quantitative phenotype" will be set forth below. For now recognize that the quantitative features of the phenotype are chosen to capture expected interesting features the cells, such as dispersed Golgi, bias toward a particular cell cycle phase, migration, cord formation, and extracellular matrix deposition. Typically, the phenotype is developed across a population of cells that have been subject to a particular set of conditions. This addresses the wide variability in phenotype for any given cell type when exposed to particular sets of conditions.

After the relevant quantitative phenotypes have been generated they are evaluated and compared to draw conclusions about the effect of the agent on the biological condition. See 113. Agent induced changes to the phenotype can be quantified and used to identify significant changes in the biological condition (e.g., arrested mitosis, increased protein synthesis, reduced migration, etc.).

Definitions

Some of terms used herein are not commonly used in the art. Other terms have multiple meanings in the art. Therefore, the following definitions are provided as an aid to understanding the description that follows. The invention as set forth in the claims should not necessarily be limited by these definitions.

The term "biological condition" refers to a particular state of an organism, an organ, a tissue, individual cells, subcellular organelles, cellular pathways and the like. Examples of such states include a disease state, a normal unperturbed state, a quiescent state, an active state, a particular state within the cell division cycle, and the like. Specific examples of biological conditions include various types of cancer, infection by various pathogens, obesity, neurodegenerative diseases, diabetes, cardiovascular disease, vascular disease and the like. Of particular interest in the context of this invention are those biological conditions that are believed to require the participation of two or more cell types. Such cell types interact to produce or maintain the condition.

The term "agent" refers to something that may influence a biological condition. Often the term will be synonymous with "stimulus" or "stimuli" or "manipulation." Agents may be materials, radiation (including all manner of electromagnetic and particle radiation), forces (including mechanical, electrical, magnetic, and nuclear), fields, and the like. Examples of materials that may be used as agents include organic and inorganic chemical compounds, biological materials such as nucleic acids, carbohydrates, proteins and peptides, lipids, various infectious agents, mixtures of the foregoing, and the like. Other specific examples of agents include non-ambient temperature, non-ambient pressure, acoustic energy, electromagnetic radiation of all frequencies, the lack of a particular material (e.g., the lack of oxygen as in ischemia), etc.

The term "phenotype" generally refers to the total appearance of an organism or cell from an organism. In the context of this invention, cellular phenotypes and their representations in processing systems (e.g., computers) are particularly interesting. A given cell's phenotype is a function of its genetic constitution and environment. Often a particular phenotype can be correlated or associated with a particular biological condition. Typically, cells undergoing a change in biological conditions will undergo a corresponding change in phenotype.

Thus, cellular phenotypic data and characterizations may be exploited to deduce mechanisms of action and other features of cellular responses to various stimuli. Such data and characterizations represent a quantitative cellular phenotype. Such quantitative phenotype may comprise multiple cellular attributes that can be collectively stored and/or indexed, numerically or otherwise. The attributes are typically quantified in the context of specific cellular markers. Measured attributes useful for characterizing an associated phenotype include geometric parameters (e.g., size, shape, and/or location of the organelle) and composition (e.g., concentration of particular biomolecules within the organelle). Other attributes include changes in a migration pattern, a growth rate, cord formation, an extracellular matrix deposition, and even cell count.

The phenotype may be characterized by exposing various cell lines to an agent of interest at various levels (e.g., doses of radiation or concentrations of a compound). In each example within this range, the attributes of interest are measured. Ultimately, certain phenotypic features (combinations of attribute values) are associated with the agent of interest. The combination of these features provides a particular quantitative phenotype. This combination is also sometimes referred to as a phenotypic fingerprint or just "fingerprint."

Particularly interesting quantitative phenotypes may be employed as "target phenotypes." These phenotypes are understood to represent a particular transition or state of a cell. For example, a target phenotype might represent a cancer cell that has a pathway relevant to the cancer state blocked or limited. In another example, a target phenotype represents a budding yeast cell that has had its microtubules depolymerized. In assessing affects of particular agents on cells, one can use target phenotypes to specifically characterize the effect of that agent in terms of mechanism of action, potency, and the like. A mathematical "distance" between a quantitative target phenotype and a phenotype under consideration, both before and after exposure to the agent, will indicate how the agent is acting. In some cases, however, simple changes in a quantitative phenotype—independent of comparison to any "target phenotype"—may indicate important events.

The term "cell type" refers to a phenotypically distinct cell. Typically, in the methods of this invention, a first cell type and a second, different, cell type are chosen for study because they interact to produce or affect a biological condition. Often they interact synergistically with respect to the condition. The two cell types are distinguished from one another by, at least, their phenotype. In some instances, they may also have different genotypes. Commonly, two cell types having the same genotype will be studied in accordance with this invention. And often both cell types will be taken from the same organ or tissue. Examples of distinct cell types include various immune system cells, various epithelial cells, stromal cells such as fibroblasts from various organs, various neurons, etc. Stromal cells are supporting cells that are mesenchymal in origin. Examples of stromal cells include fibroblasts of the connective tissue, blood elements such as macrophages, and nervous system supporting cells such as oligodendricytes and Schwann cells.

The term "microenvironment" refers to the local environment in which two or more cell types exist. In such environment, the two or more cell types may interact with and/or influence one another. This may come about by contact between the cell types, exposure to substances that the individual cell types consume or produce, etc. In addition, two or more cell types exposed to the same microenvironment may be similarly exposed to a common agent introduced to the microenvironment. In one sense, a microenvironment mimics the environment that the cells experience in vivo. In the context of this invention, a microenvironment will often refer to an in vitro environment such as a well, compartment, or insert in which two or more cell types can reside in a co-culture or other medium allowing them to interact with and/or influence one another.

Application to Exemplary Biological Conditions

1. Cancer

Various cell types may participate in producing and maintaining a cancer. Thus, it is likely that some effective therapeutic agents will simultaneously modify the functioning of the various cell types participating in the cancerous state. Traditionally, drug discovery efforts have focused on a single cell type—those cells that have become cancerous. However, certain aspects of the disease may bring different cell types into play. For example, vascularization of a tumor involves endothelial cells and possibly supporting (stromal) cells, in addition to the cancerous cells. Also, cancerous epithelial cells may induce, in some manner, endothelial cells to form blood vessels throughout a tumor. Metastasis, immune response to cancer, and other mechanisms associated with cancer, each bring into play multiple different cell types.

Increasing evidence points to certain necessary interactions between cancerous and non-cancerous cells to sustain tumor growth and/or metastasis. Tumors and their stroma have been demonstrated to interact to alter paracrine growth factor production, migration patterns, growth rates and extracellular matrix depositions. For example, cancerous epithelial cells may by some mechanism induce local non-cancerous mesenchymal cells to produce large quantities of paracrine growth factor, thereby stimulating tumor growth. By providing both cancerous epithelial cells and associated mesenchymal cells in the same microenvironment, one can test the effects of various agents on a system that exploits the known mesenchymal-epithelial interactions. This allows in vitro prediction of maximum clinical efficacy. The assumption here is that, in vivo, site-specific functional interactions between mesenchymal and epithelial cancer cells modulate the behavior of the tumors. Therefore, by demonstrating even subtle effects on the mesenchymal cells with a decent effect on the cancerous epithelial cells, a better therapeutic is identified.

For example, a given agent could directly affect cancerous epithelial cells (by killing them for example) and directly or indirectly affect non-cancerous non-epithelial cells to increase extracellular matrix deposition or by altering paracrine growth factor interactions. These affects are reflected in changes in the quantitative representation of the phenotype; e.g., changes in the size, shape, and/or composition of cellular organelles and cytoskeleton. In addition, the affects can be manifested by cell count, migration, and/or invasion (which can also be characteristics of the cells' quantitative phenotypes).

In a worst case (aggressive cancer remains unchecked), the cancerous epithelial cells (e.g. prostate tumor cells) continue to grow and invade the support matrix of the microenvironment in which they are grown. But perhaps a drug (agent) has a strong killing effect on prostate tumor cells and also causes a decrease in protein synthesis in the prostate fibroblasts (suggesting a decrease in possible growth factors). Such potential drug would likely have a greater efficacy than a drug that elicited a response in only one cell type. By using this invention to quantitatively phenotype both types of cells, as they are affected by the agent, one can more accurately predict preclinical efficacy by determining and correlating changes to a specific drug on both the cancer cells (epithelium) and on its supporting cells (e.g., fibroblasts).

In a specific preferred approach, a very potent GI50 on epithelial cells with a very potent GI50 on the mesenchyme would be too toxic, while a modest GI50 on the epithelial cells and no affect on the mesenchyme would be too ineffective. A potent or modest epithelial GI50 teamed with a modest affect on mesenchymal cells would be optimal.

The cell killing potency of an agent can be quantified by various techniques using this invention. For example, a collection of cells can be imaged immediately before exposure to the agent and then again one or more times later. An image analysis algorithm counts the living cells in each image. If the cell count does not reach an expected number after exposure to the agent the cell killing potency of the agent can be assessed. More specifically, the cell count provides the EC50 and GI50 of the agent. Important information may also be derived from the cell division cycle stage at which the growth was arrested.

The cell killing potency of the agent can also be determined by looking for characteristic phenotypes. For example, apoptosis can be detected by a fragmented nucleus. The nucleus can be visualized by staining the cell with a DNA stain such as DAPI or Hoechst 33341 available from Molecular Probes, Inc. of Eugene, Oreg. Necrosis may be detected by cell membrane disruption. The cell membrane can be visualized with a suitable stain such as FM 1-43 available from Molecular Probes, Inc. of Eugene, Oreg.

Protein synthesis can be monitored by various techniques. For example, the quantity of certain organelles associated with protein synthesis (e.g., endoplasmic reticulum and vacuoles) can be measured. An increase in the quantity of such organelles indicates an increase in protein synthesis. Similarly, a decrease in the quantity of such organelles indicates a decrease in protein synthesis. Protein synthesis can also be monitored by indicia of metabolism, such as the amount of mitochondia in a cell. Each of these measures serves as at least one component of a quantitative phenotype.

As mentioned, at least two cell types interact during vascularization of tumors. Thus, this invention can be employed to model angiogenesis and correlate drug responses of these models. Obviously, endothelial cell lines would be used in these models. In such examples, maximum clinical efficacy would be defined when a proposed therapeutic resulted has a potent GI50 on cancerous epithelial cells, a select and potent GI50 on endothelial cells (or other assays of angiogenesis), and a modest effect on the mesenchyme.

In one approach, a series of experiments is conducted. A set of control experiments is conducted with cancerous epithelial cells alone, HUVEC (human umbilical venus endothelial cells) alone, and stromal cells alone. Normally, the epithelial and stromal cells will not change significantly over time. The endothelial cells on Matrigel are expected to form cords as the precursors to blood vessels. Exposure to an agent of interest may cause changes in the expected behavior of each these cell types (as measured by analyzing images of the cells). More interestingly, epithelial cells and endothelial cells can be placed in the same microenvironment, where they interact with each other. Possibly, the epithelial cells will stimulate the endothelial cells to form cords faster, induce increased branching of the cords or cause degradation of the matrix. Also, the epithelial cells may form tight cords around the epithelial cells. Ideally, a potential therapeutic will limit the growth of the epithelial cells and the cord formation of the endothelial cells.

In another model, the cancerous epithelial cells, the endothelial cells, and the supporting fibroblasts are all provided in the same microenvironment. In the worst case, the islands of epithelial cells proliferate and invade a supporting matrix. In addition, the endothelial cells form tight cords around the epithelial cells. In the best case, the agent under consideration has a strong killing effect on the cancerous epithelial and the endothelial cells, but only a moderate effect on the fibroblasts. For example, the GI 50 values of a promising therapeutic candidate may be 100 nM for the epithelial cells, 100 nM for the endothelial cells, and 800 nM for the fibroblasts. In a separate assay, the agent could be tested against a different type of vascular cell such as aortic endothelial cells. In this example, the promising candidate might have a GI50 of 1 mM or greater for the aortic cells. In each assay/model, results are assessed from an image analysis to generate quantitative phenotypes. Cord formation can be monitored by identifying endothelial cells in an image and then determining if they align themselves in elongated groups. Such arrangements can be discerned using conventional image analysis techniques.

Metastasis is another mechanism that may be investigated using the present invention. Recent evidence suggests that some cancer cells induce their stromal cells to express substances, which attack basal membranes that might normally confine the cancer cells. For example, collagenase-3 (MMP-13) has recently been identified as a member of a gene family that is expressed in breast carcinomas and in articular cartilage from arritic patients. These investigations have found that collagenase-3 is expressed by stromal cells immediately adjacent to epithelial tumor cells but not by the tumor cells themselves. Further, it is not expressed by normal breast glandular epithelium or the associated normal stromal cells. Co-culture experiments using human fibroblasts and the MCF-7 breast cancer cells revealed that conditioned medium from breast cancer cells stimulated fibroblastic expression of collagenase-3 mRNA. See Uria et al., "Regulation of Collagenase-3 Expression in Human Breast Carcinomas is Mediated by Stromal-Epithelial Cell Interactions," Cancer Research, 1997; 57 (21): 4882-8. This result suggests that transcription of collagenase-3 in stromal cells is activated by diffusable factors released from epithelial breast cancer cells. Accordingly, collagenase-3 may be a molecular factor important in the stromal reaction to invasive breast cancer and, by concerted action, may be essential for tumor growth and progression.

In the context of this invention, a microenvironment harboring both human breast fibroblasts and MCF-7 breast cancer cells can be subjected to a potential therapeutic agent. By monitoring how such agent changes the quantitative cellular phenotype of both the human fibroblasts and the MCF-7 cells, one can predict a likely therapeutic outcome. For example, as described above, one can use the phenotype to indicate cellular movement, EC50s, and protein synthesis. Such studies may become even more valuable when coupled with an assay for the relevant factor: collagenase-3 or collagenase-3 mRNA in this example.

Another relevant interaction that can be modeled by the present invention is the interaction between cancer cells and immune cells. By co-culturing cancer cells and relevant immune cells such as macrophages, one can see how a particular agent affects the phenotypes of both cell types. Further, valuable information could be obtained by co-culturing normal cells, cancerous variants of the normal cells, and macrophages. An agent that selectively stimulates anti-cellular activity of macrophages against cancer cells, but not against normal cells, while all three cell types are co-cultured may be a valuable therapeutic.

Preferably, in most of the above-described investigations of cancer, each of the various cell lines used in this study would derive from the same site of origin; for example, prostatic epithelial cells and prostatic fibroblasts. Further, the agents being evaluated should be administered to a cell culture or other system that accurately reflects the tissue microenvironment. Very often, co-cultures may be suitable in this regard.

2. Neural Degenerative Disease

Selective cellular degeneration occurs in different cell populations in the central (CNS) and peripheral nervous system (PNS), causing different progressive, crippling and eventually fatal neurodegenerative diseases. Degeneration of the dopaminergic neurons in the substantia nigra causes Parkinson's disease; degeneration of the cholinergic neurons in the basal forebrain is associated with Alzheimer's disease; and degeneration of the cholinergic motor neurons in the brain stem and spinal cord causes amyotrophic lateral sclerosis (ALS; Lou Gehrig's disease). In these diseases, there is increasing evidence that points to interactions between the supporting cells of the CNS or PNS and the neurons themselves. These supporting cells (neuroglia) in the CNS include astrocytes, oligodendroglia, microglia and ependymal cells and in the PNS, Schwann and satellite cells. The analysis of this interaction between the neuroglia and neurons and the cell specific changes that occur after addition of possible therapeutics, in accordance with this invention, results in a better assessment of the therapeutics.

The importance of growth factors in neural development is well established and includes NGF, NT-3, NT4/5, IGF-1 and estrogen. Growth, differentiation and survival of glia and glia progenitors are influenced by PDGF, bFGF, IGF-1 and 2, NT-3, CNTF, retinoic acid, IL-6, and LIF. Most of these factors are supplied from neurons or other neuroglia. Growth factors can act on one or multiple cell types. For example, PDGF is a potent regulator of oligodendrocyte progenitor migration and proliferation, while IGF-1 acts both on neurons and myelin-forming cells to promote myelination. In vivo the balance between proliferation and differentiation appears to be controlled by different sets of growth factors locally synthesized in the CNS.

The relationship between axons and glia is reciprocal and complex. Astrocytes can block axon nerve fibers by contact. In vitro however, axons will grow on astrocyte monolayers although not in 3-dimentional cultures. Myelinating Schwann cells, which are activated and have an extensive extracellular matrix, are permissive for axonal growth both in the mammalian PNS and CNS. The ability of Schwann cells to influence regeneration derives in part from their ability to produce trophic factors including NGF, BDNF and CNTF, but also their expression of cell adhesion molecules known to promote neurite growth. In the CNS, altered levels of proteins from neuroglia which induce extracellular matrix degradation (MTI-MMP and MMP-2) have been implicated in Alzheimer's disease and multiple sclerosis.

In Parkinson's disease, a loss of 60% of substantia nigra cells results in the manifestations of clinical symptoms including bradykinesia and tremors. Current therapies are directed at replacing the deficient neurotransmitter, dopamine, or maintaining its presence by blocking its metabolism. Glial cells may also participate in the pathophysiology of this disease. Glial cells can produce trophic factors that may stimulate neural survival or produce toxic compounds that may be involved in neural degeneration. By co-incubation of the different cell types, and administering potential therapeutics, the cell specific change in the context of the complex interplay between the cell types can be assessed with the technology of this invention.

In the context of this invention, a microenvironment harboring both human brain supporting cells neuroglia and dopaminergic neural cells can be subjected to a potential therapeutic agent would be utilized for drugs for possible use in Parkinson's disease. The source of the dopaminergic cells may include, but is not limited to, neural stem cells, primary cells from the basal ganglia, limbic system, substantia nigra, hypothalamus, the medulla cortex or other cells lines of neural or adrenal origin (such as PC12). By monitoring how such agent changes the phenotype of both, neuroglia and dopaminergic neural cells one can better predict the likely therapeutic outcome. For example, certain drugs may elicit a growth factor from the neuroglia or neural cells that would act in a paracrine fashion on the other cell type to maintain a specific architecture or a healthier state.

Some examples of the functional biology to be assessed morphologically would include: general cell health of both cell types would be determined by cytoskeletal characterization (microtubule, microfilament, actin) and changes in mitochondrial number and intracellular placement of the organelles. Determination of changes in cell shape by assessment of neurite outgrowth and neuroglia extensions, and hypertrophy of each cell type. Determining tight junctional complexes between similar and different cell types would be assessed by antibodies to N-catenin and N-cadherin. The frequency and shape of processes and interconnections between cell types such as astrocyte foot process and oligodendrocyte membranous sheets would be determined. All of these morphological changes can be identified by conventional image analysis technology of the type described below.

For Parkinson's disease, the ideal therapeutic would maintain the healthiest cells types (demonstrated by cytoskeletal characterization and organelle placement) with extensive arborization of the neural cells while maintaining a healthy, but non-reactive neuroglia (as demonstrated by few extensions; no increase in the intracellular proteins GFAP or CD45).

Alzheimer's disease is characterized by progressive loss of memory and often cognitive functions due to degeneration of cholinergic neurons in the basal forebrain. The disease accounts for the vast majority of cases of senile dementia. In addition to the loss of cholinergic nerve terminals in the cerebral cortex and hippocampus, there is a severe loss of cholinergic neurons in the nucleus basalis of Meynert and related nuclei that contain the cell bodies of cholinergic neurons which project to the hippocampus, the amygdala, and all the neocortex. The cause of the degeneration of the cholinergic neurons in Alzheimer's is unknown. However, cytopathological hallmarks include alterations in both nerve fibers and reactive glial cells.

In the context of this invention, a microenvironment harboring both neuroglia and neural cells can be subjected to a potential therapeutic agent would be utilized for Alzheimer's disease. The interaction between the divergent cell types can give a better assessment of the likely therapeutic outcome. The source of the basal forebrain cells may include, but is not limited to, neural stem cells, primary cells from the basal forebrain, hippocampus, neocortical regions, or cells lines of neural origin. By monitoring how such agents change the phenotype of both, neuroglia and cholinergic neural cells one can better predict the likely therapeutic outcome. As in the Parkinson's example, certain drugs may elicit a growth factor or toxic factor from the neuroglia or neural cells that would act in a paracrine fashion on the other cell type to maintain or compromise its architecture or health status.

It is important to assess the changes in both cell types simultaneously after administration of potential drugs. To be assessed morphologically would include cell shape that would include arborization of the neural cell body (neurite outgrowth) and neuroglia body, and hypertrophy of each cell type. The formation of tight junctions between the different cell types including N-catenin and N-cadherins, and processes such as astrocyte foot process and oligodendrocyte membrane sheets. The health of both cell types would be determined by cytoskeletal characterization (microtubule, microfilament, actin) and changes in mitochondrial number and intracellular organelle placement.

For Alzheimer's disease, the ideal therapeutic would maintain the healthiest neural cells types with arborization and maintain a healthy but non-reactive neuroglia (few extensions; no increase in GFAP or CD45) with particular emphasis on maintaining a non-reactive astrocyte population.

Amyotrophic lateral sclerosis (ALS; Lou Gehrig's disease) is a progressive disease characterized by gradual degeneration of the motor neurons in the spinal cord and brain stem. The progressive neural loss eventually results in a severe muscular weakness and wasting, increasing difficulty in breathing and swallowing, with many sufferers become victims of pneumonia.

In the context of this invention, a microenvironment harboring both human peripheral supporting cells (Schwann and satellite cells) and neural CNS or PNS can be subjected to a potential therapeutic agent would be utilized for cell maintenance. By monitoring how such agent changes the phenotype of both, supporting cells and peripheral neural cells, one can better define a successful therapeutic outcome. The source of the motor neuron cell may include, but is not limited to, neural stem cells, primary cells from the spinal cord, or motor cells lines of neural origin. By monitoring how such agents change the phenotype of both neuroglia and motor neurons cells one can better predict the likely therapeutic outcome. Certain drugs may elicit a growth factor or toxic factor from the neuroglia or neural cells that would act in a paracrine fashion on the other cell type to maintain or compromise its architecture or a healthier state.

Similar to the Parkinson's example, co-culture of these cells would result in a combination of effects with the neural neuroglia interplay. The ideal effect that would define a useful therapeutic would include that the motor neurons should maintain a healthy phenotype as demonstrated by proper organelle placement and number, cytoskeletal maintainence and numerous arboreal extensions. Proper organelle placement and number, cytoskeletal maintainence of cell shape, and a population responsive to known growth factors would complete the ideal phenotype for the Schwann cells.

3. Cardiac Disease

Heart failure in one of the leading causes of death in the United States. Although myocardial infarction may result in substantial loss of functional myocardium and lead to acute cardiac decompensation, it is now well recognized that the subsequent changes in the noninfarcted myocardium play an important role in the longer term. This process, which involves changes in myocytes (hypertrophy, dysfunction) and in the extracellular matrix (ECM), has been termed remodeling.

In vitro hypoxia induces apoptosis in cardiac myocytes but does not cause apoptosis in cardiac fibroblasts. At the molecular level, an increase in ECM proteins is observed in the chronically ischemic heart that are produced predominately by cardiac fibroblasts that surround the cardiac myocytes. Overproduction of the ECM eventually results in adverse effects on the contractility of the myocardium. A wide variety of growth factors can regulate cell proliferation and ECM synthesis. One of these growth factors is connective tissue growth factor (CTGF). Significant upregulation of CTGF is detected in human heart samples derived from patients diagnosed with cardiac ischemia and in animal models of myocardial infarction. CTGF expression is regulated by TGF-b in both cardiac fibroblasts and cardiac myocytes.

There are significant increases in mRNA expression of several proinflammatory cytokines and growth factors by cardiac nonmyocyte cells isolated from the noninfarcted myocardium. It is likely that these cytokines and growth factors produced by the nonmyocytes play an important role in postinfarct myocytes hypertrophy and contractile protein expression. This highlights the importance of examining cell specific changes within the context of cell to cell interactions. Alterations in nonmyocytes may be involved in the mechanism by drugs such as angiotensin-converting enzyme inhibitors favorably impact on the postinfarction remodeling process.

In the context of this invention, a microenvironment harboring both human nonmyocyte cells and cardiac myocytes can be subjected to a potential therapeutic agent and the cell specific responses within the context of cell to cell interaction can be evaluated. By monitoring how such agent changes the phenotype of both, one can better define a successful therapeutic. The source of the nonmyocytes cell may include, but is not limited to, stem cells, primary cells, fibroblasts and endothelial cells lines of cardiac origin. The source of myocytes may include, but is not limited to primary fetal, neonatal and adult human and animal ventricular myocytes, stem cells, and atrial and ventricular cardiac cell lines and cell lines derived from other sources including skeletal and smooth muscle.

In one example, certain drugs may protect the cardiac cells from hypoxia but induce cytokines release from myocytes and nonmyocytes that would act in a paracrine and autocrine fashion on the nonmyocytes cells to initiate fibrosis and subsequent pathology. This would not be an ideal therapeutic. The ideal cell phenotypes induced by a possible therapeutic would maintain healthy responsive cardiac myocytes as demonstrated by cytoskeletal characterization, organelle placement and intracellular calcium levels, but with no proliferation of the nonmyocyte cells, and maintaining a low and constant amount of the protein synthesis machinery (ER and Golgi) within the cell.

4. Other Biological Conditions

The above examples are by no means the only conditions that may be analyzed via the methods of this invention. Another example is auto-immune disease, which may be investigated using one cell type that is an immune system cell and a second cell type that is attacked by cells of the first cell type in the auto-immune disease. In another example, the biological condition is Type II diabetes. This condition may be investigated with a first cell type that is a muscle cell and a second cell type is an adipocyte cell type, an immune cell type, or a vascular cell type.

Markers and Descriptors for the Quantitative Phenotype

Regarding quantitative phenotypes, a compound or other agent is analyzed in terms of its effect on the two or more interacting cell lines. More specifically, the compound is linked to a particular phenotype for each of these cell lines. Two or more values or measures of cellular attributes characterize each phenotype. These attributes are quantified in the context of specific cellular markers, as described below.

The phenotype may be characterized by administering a compound of interest in various concentrations to the two or more interacting cell lines. In each example within this matrix, the attributes of interest are measured. Ultimately, certain phenotypic features (combinations of attribute values) are associated with the compound of interest. These features provide a template for the phenotype. Particular quantitative phenotypes can be characterized by comparison to known quantitative phenotypes. These other quantitative phenotypes appear only when a particular condition occurs; e.g., a compound acts according to an associated mechanism of action that results in a phenotypic signature.

The known phenotypes may also be generated by genetic alteration via a genetic or epigenetic process that affects the expression level or activity of a particular protein. In the context of drug discovery, a gene encoding for a particular target can be genetically knocked out, under expressed, over expressed, expressed in a non-native state, etc. More generally, any cellular stimulus (e.g., radiation level and type, gravity level, magnetic field, acoustic perturbations, etc.) can be used to generate the cell line of interest. Importantly, this stimulus affects the phenotype and can be correlated therewith.

This may be accomplished via standard procedures involving genomic modification, translation or transcription apparatus modification (e.g., use of antisense nucleic acids), blocking target activity (using antibodies to a receptor site for example), and the like. These processes will generally affect the phenotype in some quantifiable way. Importantly, they clearly and unambiguously define a cellular phenotype associated with altering the activity of the target protein.

Analyzing biological conditions based upon phenotype can take many paths. Most will involve some mathematical basis. For example, the phenotype defined at can be represented as a fingerprint or vector comprised of multiple scalar values of cellular attributes (as described above). The phenotype representation can then be compared against known phenotypes characterized by the same format (e.g., they are all characterized as vectors having the same attribute set, but with different values of the attributes). The comparison may be as simple as an Euclidean distance or more sophisticated as a neural network or multivariate statistical correlation.

The known compounds and associated phenotypes may be stored as database records or other data structures that can be queried or otherwise accessed as part of the identification procedure. The compounds may also be associated with other relevant data such as clinical toxicity, cellular toxicity, hypersensitivity, mechanism of action, etc. (when available).

Figure 2:
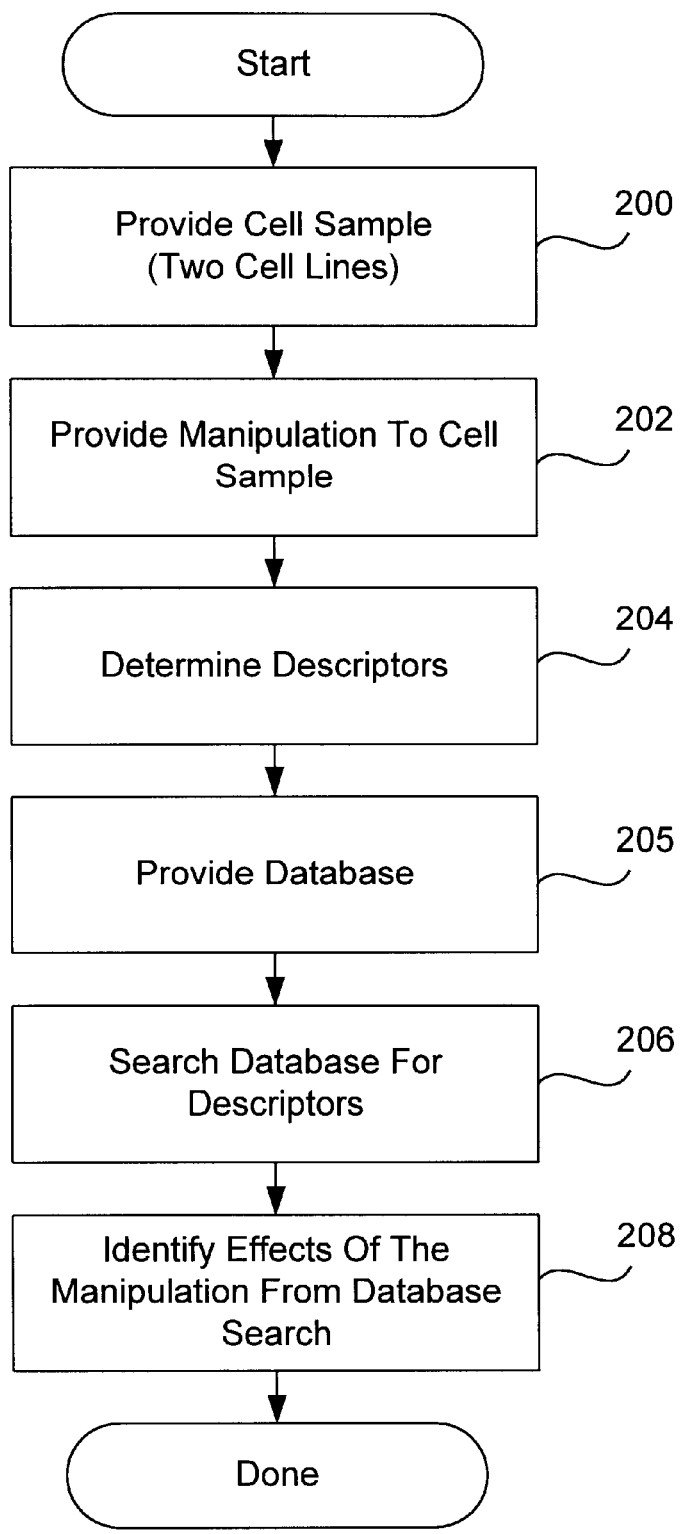
FIG. 2 is a process flow diagram showing a procedure generating and using a quantitative phenotype.

FIG. 2 illustrates a representative block flow diagram of simplified process steps of a method for developing quantitative phenotypes resulting from the effects of an agent on one or more portions of one or more cells. This diagram is merely an illustration and should not limit the scope of the claims herein. One of ordinary skill in the art would recognize other variations, modifications, and alternatives. In operation 200, the two interacting cell types are provided. At this point, the cells can be live, dead, or fixed cells, or cell fractions. The cells also can be in one of many cell cycle stages, including G0, G1, S, G2 or M phase, M phase including the following cell cycle stages: interphase, prophase, prometaphase, metaphase, anaphase, and telophase.

Cell markers tracked in presently preferable embodiments can include proteins, protein modifications, genetically manipulated proteins, exogenous proteins, enzymatic activities, nucleic acids, lipids, carbohydrates, organic and inorganic ion concentrations, sub-cellular structures, organelles, plasma membrane, adhesion complex, ion channels, ion pumps, integral membrane proteins, cell surface receptors, G-protein coupled receptors, tyrosine kinase receptors, nuclear membrane receptors, ECM binding complexes, endocytotic machinery, exocytotic machinery, lysosomes, peroxisomes, vacuoles, mitochondria, Golgi apparatus, cytoskeletal filament network, endoplasmic reticulum, nuclear membrane, proteosome apparatus, chromatin, nucleolus, cytoplasm, cytoplasmic signaling apparatus, microbe specializations and plant specializations.

The following table illustrates some markers and cell components that may be used in embodiments of the present invention. Other markers can be used in various embodiments without departing from the scope of the invention.

| Cell component | Marker | Disease State |
|---|---|---|
| Plasma membrane (including overall cell shape) | Carbocyanine dyes Phosphatidylserine Various lipids Glycoproteins | Apoptosis—Cancer Apoptosis—Neural degenerative Ds |
| Adhesion complexes | Cadherins Integrins Occludin Gap junction ERM proteins CAMs Catenins Desmosomes | Thrombosis Metastasis Wound healing Inflammatory Ds Dermatologic Ds |
| Ion Channels and Pumps | Na/K Atpase Calcium channels Serotonin reuptake pump CFTR SERCA | Cystic fibrosis Depression Congestive Heart Failure Epilepsy |
| G coupled receptors | β adrenergic receptor Angiotensin receptor | Hypertension Heart Failure Angina |
| Tyrosine kinase receptors | PDGF receptor FGF receptor IGF receptor | Cancer Wound healing Angiogenesis Cerebrovascular Ds |
| ECM binding complexes | Dystroglycan Syndecan | Muscular Dystrophy |
| Endocytotic machinery | Clathrin Adaptor proteins COPs Presenilins Dynamin | Alzheimer's Ds |
| Exocytotic machinery | SNAREs Vesicles | Epilepsy Tetanus Systemic Inflammation Allergic Reactions |
| Lysosomes | Acid phosphatase Transferrin Lysotracker Red | Viral diseases |
| Peroxisomes/ Vacuoles | | Neural degenerative Ds |
| Mitochondria | Caspases Apoptosis inducing factor F1 ATPase | Apoptosis Neural degenerative Ds Mitochondrial Cyto- pathies |
| | Fluorescein Cyclo-oxygenase Mitotracker Red Mitotracker Green | Inflammatory Ds Metabolic Ds |
| Golgi Apparatus | Lens Culinaris DiOC6 carbocyanine dye COPs Antibodies specific for Golgi | |

| Cell component | Marker | Disease State |
|---|---|---|
| Cytoskeletal Filament Networks | Microtubules Actin Intermediate Filaments Kinesin, dynein, myosin Microtubule associated proteins Actin binding proteins Rac/Rho Keratins GFAP Von Wiltbrand's factor | Cancer Neural degenerative Ds Inflammatory Ds Cardiovascular Ds Skin Ds |
| Endoplasmic Reticulum | SNARE PDI Ribosomes | Neural degenerative Ds |
| Nuclear Membrane | Lamins Nuclear Pore Complex | Cancer |
| Proteosome Apparatus | Ubiquityl transferases | Cancer |
| Chromatin | DNA Histone proteins Histone deacetylases Telomerases | Cancer Aging |
| Nucleolus | Phase markers | |
| Cytoplasm | Intermediary Metabolic Enzymes BRCA1 | Cancer |
| Cytoplasmic Signaling Appartus | Calcium Camp PKC pH | Cardiovascular Ds Migraine Apoptosis Cancer |
| Microbe Specializations | Flagella Cilia Cell Wall components: Chitin synthase | Infectious Ds |
| Plant specializations | Choloroplast Cell Wall components | Crop Protection |

At 202, each of the two or more interacting cell lines is manipulated. Such manipulations represent exposure to agents or stimuli as described above. In general, relevant manipulations can comprise exposure to one or any combination of chemical, biological, mechanical, thermal, electromagnetic, gravitational, nuclear, or temporal factors, for example. For example, manipulations could include exposure to chemical compounds, including compounds of known biological activity such as therapeutics or drugs, or also compounds of unknown biological activity. Or exposure to biologics that may or may not be used as drugs such as hormones, growth factors, antibodies, or extracellular matrix components. Or exposure to biologics such as infective materials such as viruses that may be naturally occurring viruses or viruses engineered to express exogenous genes at various levels. Bioengineered viruses are one example of manipulations via gene transfer. Other means of gene transfer are well known in the art and include but are not limited to electroporation, calcium phosphate precipitation, and lipid-based transfection. Manipulations could also include delivery of antisense polynucleotides by similar means as gene transfection. Other genetic manipulations include gene knock-outs or gene mutations. Manipulations also could include cell fusion. Physical manipulations could include exposing cells to shear stress under different rates of fluid flow, exposure of cells to different temperatures, exposure of cells to vacuum or positive pressure, or exposure of cells to sonication. Manipulations could also include applying centrifugal force. Manipulations could also include changes in gravitational force, including sub-gravitation. Manipulations could include application of a constant or pulsed electrical current. Manipulations could also include irradiation. Manipulations could also include photobleaching, which in some embodiments may include prior addition of a substance that would specifically mark areas to be photobleached by subsequent light exposure. In addition, these types of manipulations may be varied as to time of exposure, or cells could be subjected to multiple manipulations in various combinations and orders of addition. Of course, the type of manipulation used depends upon the application.

At 204, one or more descriptors of a state in the portions of the cells in the presence of the manipulation can be determined using the images collected on the imaging system. Descriptors can comprise scalar or vector values, representing quantities such as geometric parameters (e.g., size, shape, and/or location of the organelle) and composition (e.g., concentration of particular biomolecules within the organelle, as represented by intensity and gray level, for example).

Other types of descriptors include, but are not limited to, one or any combination of characteristics such as a cell count, an area, a perimeter, a length, a breadth, a fiber length, a fiber breadth, a shape factor, a elliptical form factor, an inner radius, an outer radius, a mean radius, an equivalent radius, an equivalent sphere volume, an equivalent prolate volume, an equivalent oblate volume, an equivalent sphere surface area, an average intensity, a total intensity, an optical density, a radial dispersion, and a texture difference. These descriptors can be average or standard deviation values, or frequency statistics from the descriptors collected across a population of cells. These descriptors can be further reduced using other methods such as principal component analysis and the like. In some embodiments, the descriptors include features from different cell portions or cell types. That is, a first feature can be from a nuclei and a second feature is from another cell structure such as Golgi apparatus, mitochondria, spacing between cell structures or cells themselves, as well as many others.

The quantitative phenotypes employed in this invention may include any descriptor that represents some aspect of the appearance of a cell. Examples of some descriptors that have been found suitable are included in the following table. Other descriptors can also be used without departing from the scope of the invention.

| Name of Parameter | Explanation/Comments |
|---|---|
| Count | Number of objects |
| Area | |
| Perimeter | |
| Length | X axis |
| Width | Y axis |
| Shape Factor | Measure of roundness of an object |
| Height | Z axis |
| Radius | |
| Distribution of Brightness | |
| Radius of Dispersion | Measure of how dispersed the marker is from its centroid |
| Centroid location | x-y position of center of mass |
| Number of holes in closed objects | Derivatives of this measurement might include, for example, Euler number (= number of objects − number of holes) |
| Elliptical Fourier Analysis (EFA) | Multiple frequencies that describe the shape of a closed object |
| Wavelet Analysis | As in EFA, but using wavelet transform |
| Interobject Orientation | Polar Coordinate analysis of relative location |
| Distribution Interobject Distances | Including statistical characteristics |
| Spectral Output | Measures the wavelength spectrum of the reporter dye. Includes FRET |
| Optical density | Absorbance of light |
| Phase density | Phase shifting of light |
| Reflection interference | Measure of the distance of the cell membrane from the surface of the substrate |
| 1, 2 and 3 dimensional Fourier Analysis | Spatial frequency analysis of non closed objects |
| 1, 2 and 3 dimensional Wavelet Analysis | Spatial frequency analysis of non closed objects |
| Eccentricity | The eccentricity of the ellipse that has the same second moments as the region. A measure of object elongation. |
| Long axis/Short Axis Length | Another measure of object elongation. |
| Convex perimeter | Perimeter of the smallest convex polygon surrounding an object |
| Convex area | Area of the smallest convex polygon surrounding an object |
| Solidity | Ratio of polygon bounding box area to object area. |
| Extent | proportion of pixels in the bounding box that are also in the region |
| Granularity | |
| Pattern matching | Significance of similarity to reference pattern |
| Volume measurements | As above, but adding a z axis |

At 205, a database of cell information can be provided to allow characterization of the quantitative phenotypes at issue. Next, at 206, a plurality of quantitative phenotypes can be searched from a database of cell information in order to locate interesting stored phenotypes based upon one of the phenotypes generated by the manipulation. Then, at 208, effects of the manipulation are predicted based upon the properties of the located phenotypes. Properties can comprise toxicity, specificity against a subset of tumors, mechanisms of chemical activity, mechanisms of biological activity, structure, adverse biological effects, biological pathways, clinical effects, cellular availability, pharmacological availability, pharmacodynamic properties, clinical uses and indications, pharmacological properties, such as absorption, excretion, distribution, metabolism and the like.

In a particular embodiment, operation 206 comprises determining matching descriptors in the database corresponding to a prior administration of the manipulation to the descriptors of the present administration of the manipulation. In a particular embodiment according to the present invention, combinations of measurements of scalar values can provide predictive information. A database can be provided having one or more "cellular fingerprints" comprised of descriptors of cell-substance interactions of drugs having known mechanisms of action with cells. Such descriptors can be analyzed, classified, and compared using a plurality of techniques, such as statistical classification and clustering, heuristic classification techniques, a technique of creating "phylogenetic trees" based on various distance measures between descriptors from various drugs. In this embodiment, numeric values for the descriptors can be used by comparison techniques. A phylogenetic tree can be created that illustrates a statistical significance of the similarity between descriptors for the drugs in the database. Because the drugs used to build the initial database are of known mechanism, it can be determined whether a particular scalar value in a descriptor is statistically predictive. Finally, a compound descriptor with no known mechanism of action can be queried against the database and be statistically compared and classified among the drugs in the database that the compound most resembles.

In a particular embodiment, relationships between measured morphological properties of images and physiological conditions can be determined. Relationships can include, for example, treatment of different cell lines with chemical compounds, or comparing cells from a patient with control cells, and the like. In a presently preferred embodiment, comparisons can be performed on acquired image features. Some embodiments can comprise statistical and neural network—based approaches to perform comparisons of various features. The foregoing is provided as merely an example, and is not intended to limit the scope of the present invention. Other techniques can be included for different types of data.

In some embodiments, classification, clustering and other types of predictive data analysis can be performed on features extracted from cell images. In a presently preferable embodiment, statistical procedures for comparisons, classification and clustering are performed on data obtained from imaging cells. Embodiments can perform such analysis based upon factors such as numerical value, statistical properties, relationships with other values, and the like.

Markers can be from any of a large variety of normal and transformed cell lines from sources such as for example, human beings, fungi, or other species. The markers can be chosen to cover many areas of cell biology, such as, for example markers comprising the cytoskeleton of a cell. The cytoskeleton is one of a plurality of components that determine a cell's architecture, or "cytoarchitecture". A cytoarchitecture comprises structures that can mediate most cellular processes, such as cell growth and division, for example. Because the cytoskeleton is a dynamic structure, it provides a constant indication of the processes occurring within the cell. The cytoarchitecture of a cell can be quantified to produce a one or more scalar values corresponding to many possible cellular markers, such as cytoskeleton, organelles, signaling molecules, adhesion molecules and the like. Such quantification can be performed in the presence and absence of drugs, peptides, proteins, anti-sense oligonucleotides, antibodies, genetic alterations and the like. Scalar values obtained from such quantification can provide information about the shape and metabolic state of the cell.

In a presently preferred embodiment, scalar values can comprise morphometric, frequency, multi-dimensional parameters and the like, extracted from one or more fluorescence images taken from a number of cellular markers from a population of cells. Two or more such scalar values extracted from a plurality of cell lines and markers grown in the same condition together comprise a unique "fingerprint" or quantitative phenotype that can be incorporated into a database. Such cellular phenotypes will change in the presence of drugs, peptides, proteins, antisense oligonucleotides, antibodies or genetic alterations. Such changes can be sufficiently unique to permit a correlation to be drawn between similar phenotypes. Such correlations can predict similar properties or characteristics with regard to mechanism of action, toxicity, animal model effectiveness, clinical trial effectiveness, patient responses and the like. In a presently preferred embodiment, a database can be built from a plurality of such phenotypes from different cell lines, cellular markers, and compounds having known mechanisms of action (or structure, or gene response, or toxicity).

The present invention also employs database to facilitate quantitative phenotype comparisons. Once a set of features/descriptors has been extracted, the feature set may be used to populate a database. Accordingly, the database includes many sets of features, where each set corresponds to a different manipulation for a selected cell. A database can be provided having one or more quantitative phenotypes of cell substance interactions for drugs having known mechanisms of action with cells. Such phenotypes can be compared against those generated during multi-cell type experiments of this invention using a variety of algorithms. Such algorithms can comprise techniques for statistical classification, statistical clustering, distance based clustering, linear and non-linear regression analysis, self-organizing networks, rule-based classification, etc. One may also employ a technique of creating "phylogenetic trees" of a statistical similarity between the fingerprints from various drugs.

In some cases the extracted features may be viewed as simple features, from which composite features can be generated. Such composite features are sometimes more convenient to store and/or visualize than a collection of simple features. More than one simple feature can be combined in a variety of different ways to form these composite features. In particular, the composite feature can be any function or combination of a simple feature and other composite features. The function can be algebraic, logical, sinusoidal, logarithmic, linear, hyperbolic, statistical, and the like. Alternatively, more than one simple feature can be combined in a functional manner (e.g., arithmetic, algebraic). As merely an example, the composite feature equals a sum or product of feature 1 and feature 2, where these features correspond to the same manipulation.

Microenvironments

Figure 3A:
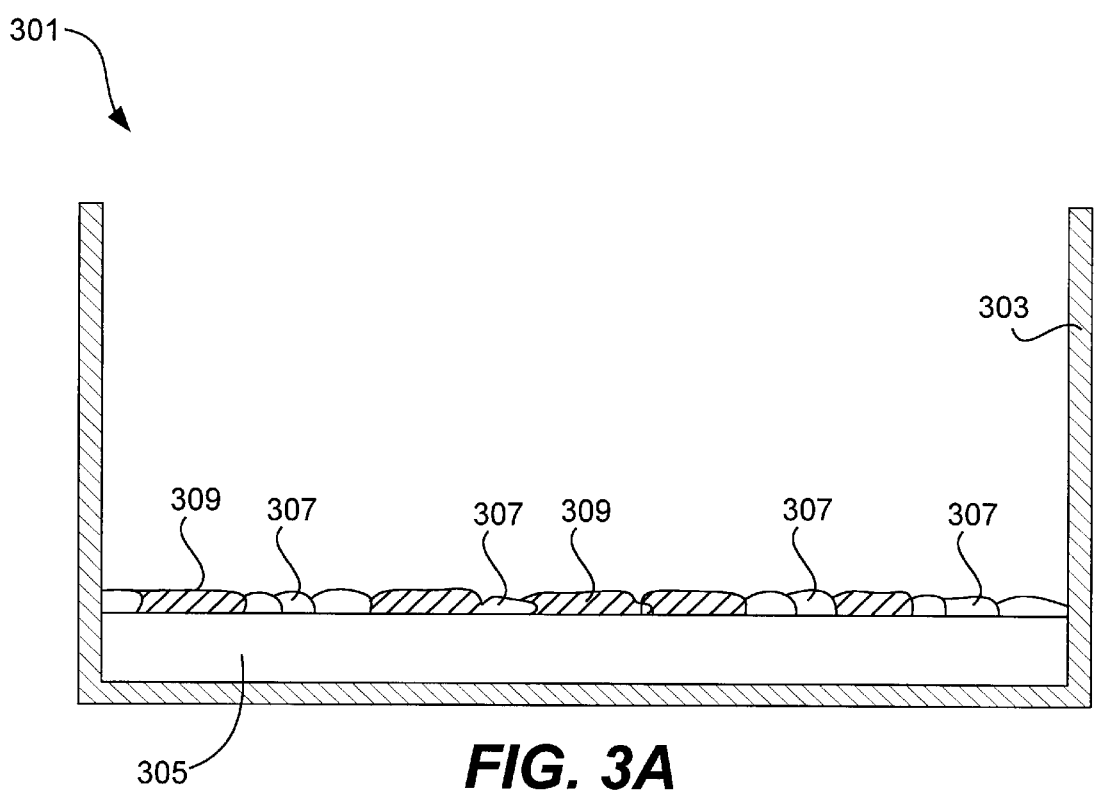
FIG. 3A is a cross-sectional view of a simple plate in which two separate cell lines are growing and interacting.
Figure 3B:
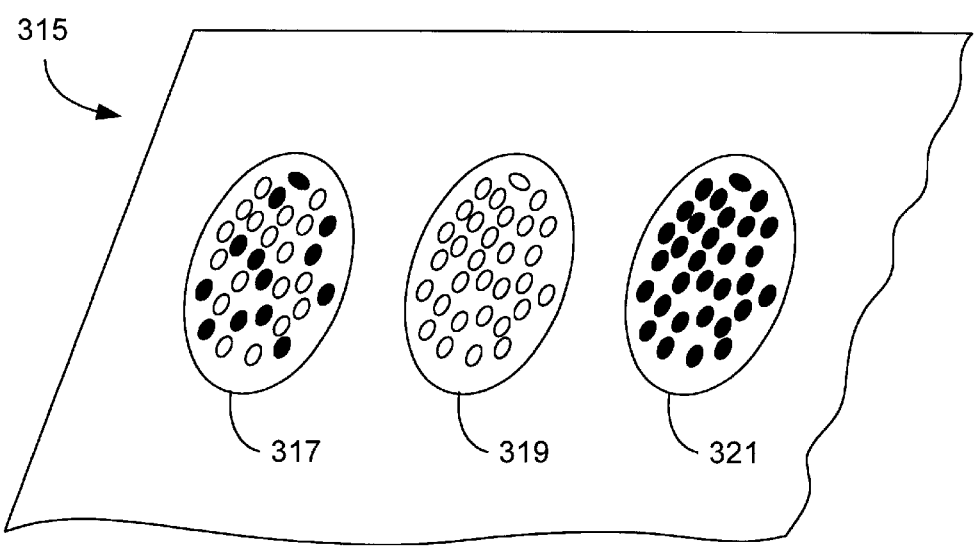
FIG. 3B is a top view of an assay plate having some wells which hold cells of only single cell types and another well that holds cells from two or more different and interacting cell types.

As mentioned, it is generally preferable to have the first and second cell lines interact prior to, during, and after administering a test compound or other agent. Various cell support designs allow this. In a simple design, cells from two different cell lines are simply plated together on a flat surface of a support vessel such as a well of an plate. FIGS. 3A and 3B depict this scenario. As shown in FIG. 3A, a cell culture device 301 includes a rigid support structure 303 such as a polymeric cup-shaped (or generally concave) structure. This structure may be fabricated from any structurally suitable and inert material such as polycarbonate, polypropylene, polyvinyl chloride, etc. At the base of structure 303 a layer of cell growth support matrix such as a feeder layer or "Matrigel" matrix (Becton-Dickinson, Franklin Lakes, N.J.). The additives necessary to support cell growth are well known to those of skill in the art. On the support matrix, cells 307 of a first cell type and cells 309 of a second cell type are growing and interacting. As indicated above, the interaction may include contact interactions and exposure to factors produced by the other cell type(s). The support matrix 305 may be chosen to facilitate such interaction.

One parameter to consider in controlling the microenvironment is the relative percentages of the different cell types. Preferably, the percentages are chosen to reflect the in vivo environment of the cells. For example, an investigation of Parkinson's disease might employ a microenvironment in which the ratio of neurons to neuroglial cells matches that of the substantia nigra. Another factor to consider is the degree to which the cells are dispersed or localized in the microenvironment. If the cells of the cell types are tightly coupled during in vivo, then the microenvironment should allow such coupling. If the cells are widely separated by extracellular matrix or the like, then the microenvironment should also allow such separation. Another factor of relevance is the relative timing of the introduction of the two or more cell types. In some designs, the cells of the first cell type are added prior to the second cell type. This may represent the actual stages of a biological condition such as tumor growth.

FIG. 3B depicts a plate having multiple wells, some of which are control wells. As shown in the figure, a plate section 315 includes three wells: well 317, control well 319, and control well 321. Each well has a different group of cells. Control well 319 contains only cells of a first cell type. Control well 321 contains only cells of a second cell type. But well 317 includes cells from both cell types. Images taken from all three wells can be compared to determine the effect of the interaction between the cell types. For example if the cells of the first cell type growing well 317 have a significantly different phenotype than the cells growing in control well 319, then it can be deduced that the interaction between the two cell types is significant. A potential therapeutic that addresses this interaction is likely be superior to one that does not.

Figure 4:
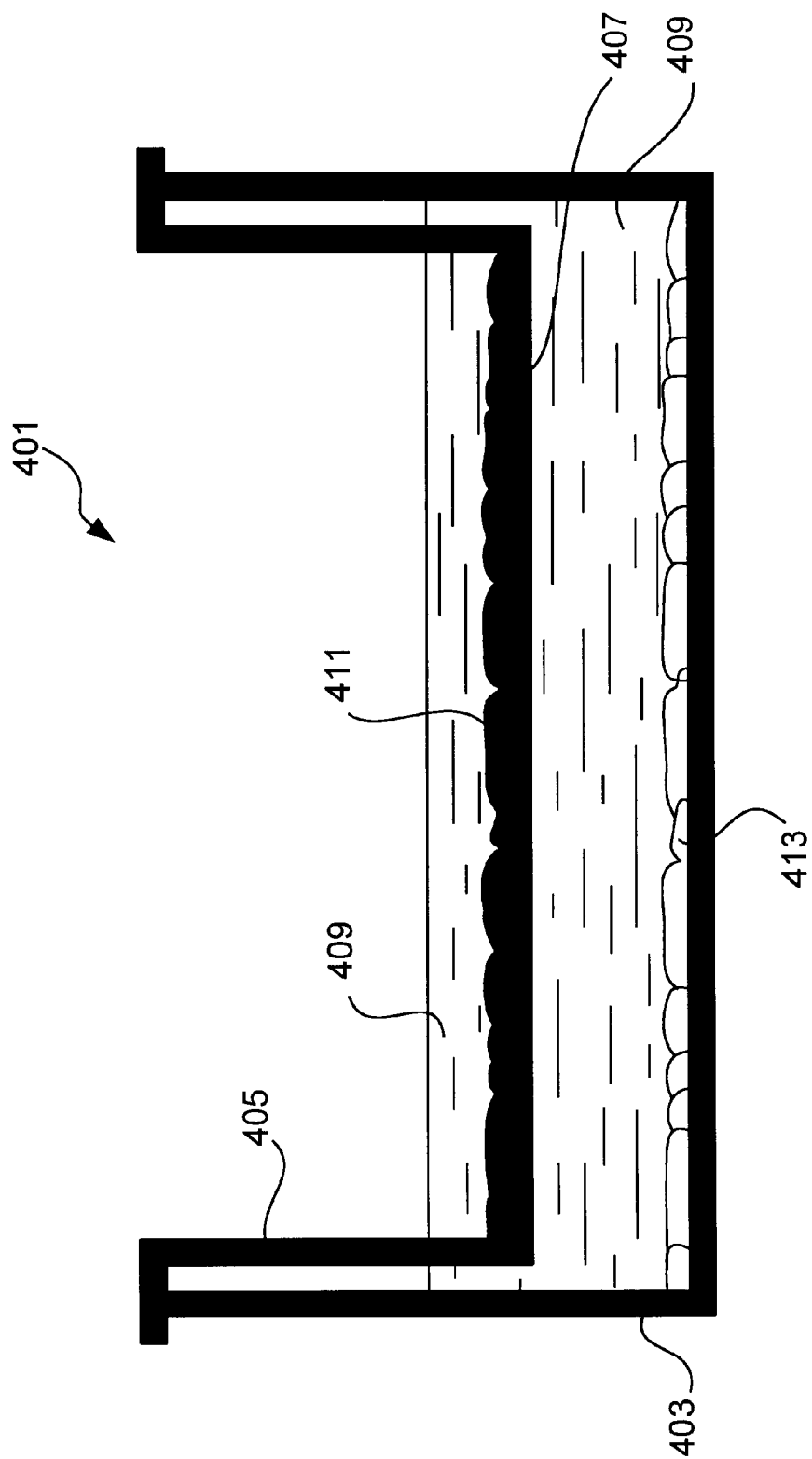
FIG. 4 is a cross-sectional view of an "insert" type microenvironment for co-culturing two different cell lines but preventing them from contacting one another.

FIG. 4 depicts another microenvironment of this invention. This microenvironment maintains respective cell lines in discrete locations (flat planes) but allows them to interact through soluble factors and other species. In this figure, a cell culture device 401 includes an outer rigid support 403 and an insert (support) 405. As shown, insert 405 rests cleanly within the interior of support 403. The bases of supports 403 and 405 rest in close proximity to one another—e.g., within 1–5 millimeters. Each of supports 403 and 405 support a different cell line. In this example, support 403 supports a first cell line 411 and support 405 supports a second cell line 413. A three-dimensional layer of support media 409 (e.g., Matrigel) contacts both cell lines 411 and 413. This allows factors produced by the individual cell lines to diffuse to the other cell lines and influence their growth. Note that the base of insert 405 includes a filter 407 or other porous support that is rigid and fine enough to prevent cell movement, but porous enough to allow easy ingress and egress of factors. In one embodiment, a simple insert-type cell culture device is the "Transwell" available from Corning Life Sciences, Acton, Mass.

Figure 5A:
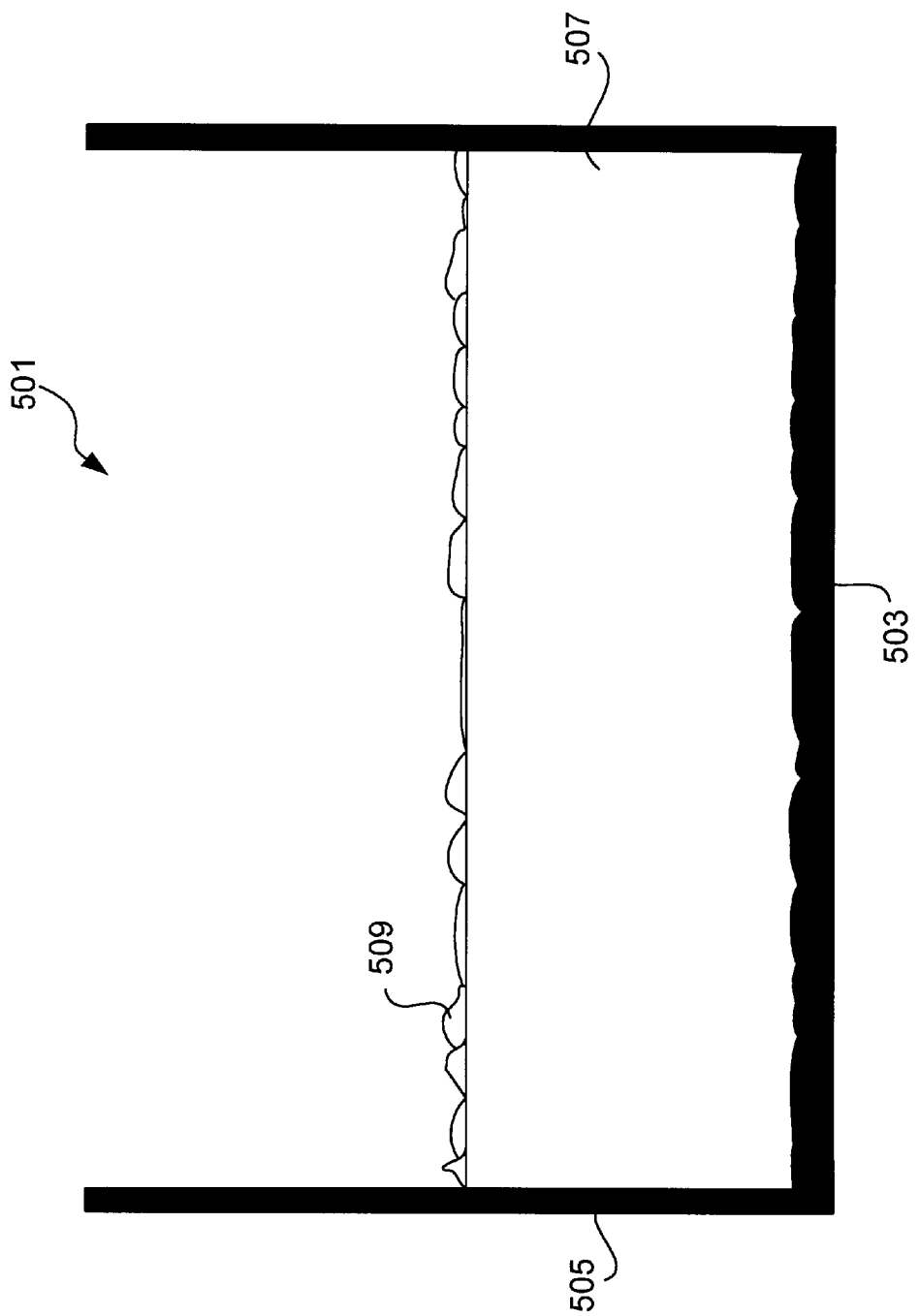
FIG. 5A is a cross-sectional view of three-dimensional microenvironment having two separated cell lines at the beginning of an experiment.
Figure 5B:
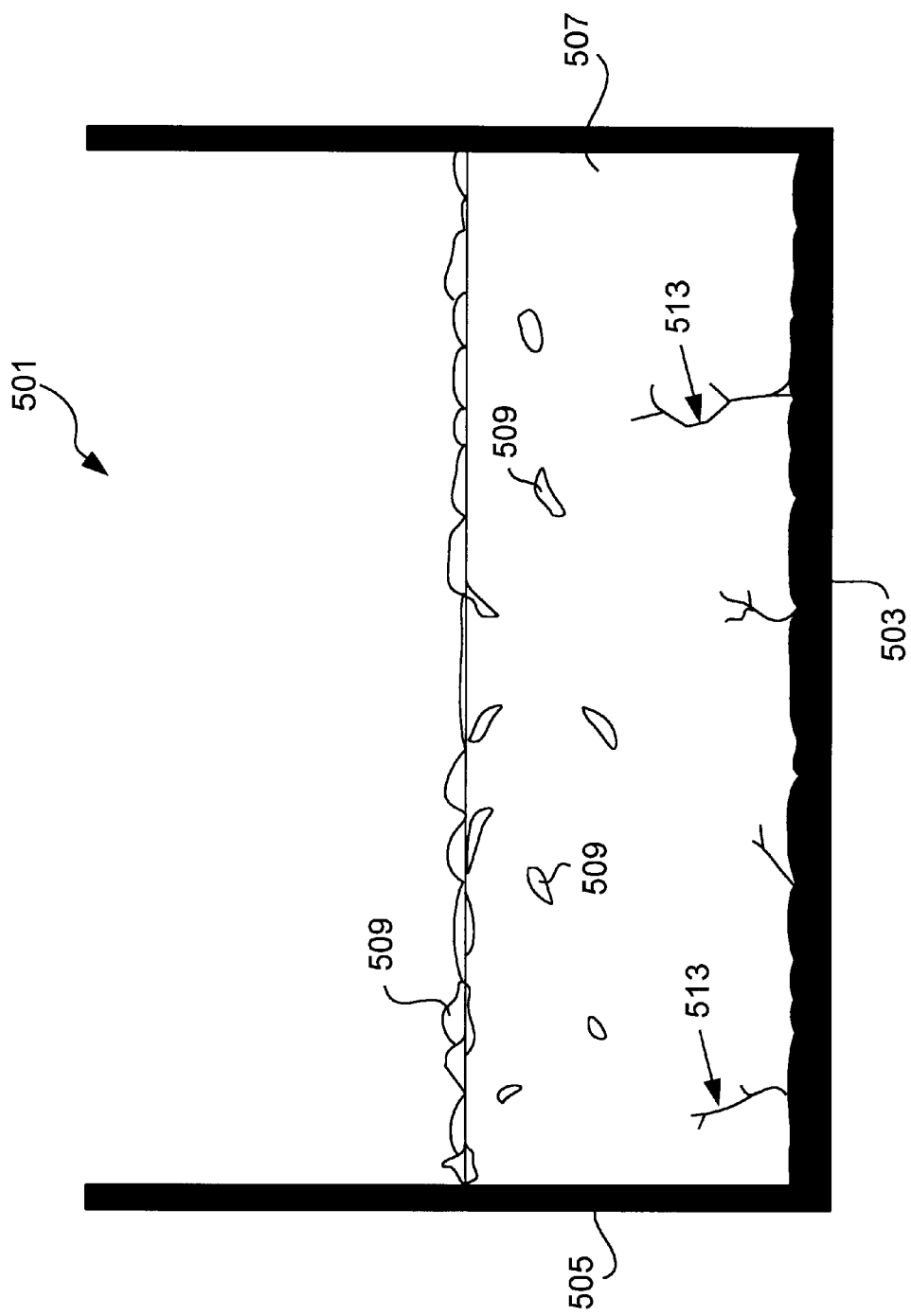
FIG. 5B is a cross-sectional view of the microenvironment of FIG. 5A, after some time has elapsed and the initially separated cell lines have moved in a third-dimension, toward each other and away from their initial positions.

Another microenvironment initially provides cells of the first and second cell types at separate locations, but allows them to move in three dimensions over the coarse of time. In some cases, this will demonstrate cell migration (relevant to metastasis for example), cell motility, and/or dendrite growth (of relevance in studying neurological conditions). FIGS. 5A and 5B depict a microenvironment 501 in which cells are initially separated, but allowed to move over time.

As shown in FIG. 5A, cells of a first cell line 503 initially reside as a flat layer at the base of a rigid container 505. A layer of three-dimensional support/growth medium 507 (e.g., Matrigel) fills the lower portion of rigid container 505. Initially, as shown in FIG. 5A, cells of the second cell type 509 reside as a flat layer on top of support medium 507.

Thus, the cells of the two cell lines are separated as two dimensional layers but allowed to interact via soluble factors, etc.

Turning now to FIG. 5B, at some later time, the cells have been growing and moving. As shown, in this hypothetical example, some cells of first cell line 503 have grown dendrites 513 that reach upward toward the cells of the second cell line 509. In addition, some cells of the second cell line 509 have begun to migrate downward, through the support medium 507, toward the cells of the first cell line 503. Dendrites and migration patterns may be identified by image analysis in the vertical direction. This information can be used as separate descriptors to be incorporated in the quantitative phenotypes of the respective cell lines.

Software/Hardware

Generally, embodiments of the present invention employ various processes involving data stored in or transferred through one or more computer systems. Embodiments of the present invention also relate to an apparatus for performing these operations. This apparatus may be specially designed and constructed for the required purposes, or it may be a general-purpose computer selectively activated or configured by a computer program, programmed logic, and/or data structure stored in the Computer, The processes presented herein are not inherently related to any particular computer or other apparatus. In particular, various general-purpose machines may be used with programs written in accordance with the teachings herein, or it may be more convenient to construct a more specialized apparatus to perform the required method steps. A particular structure for a variety of these machines will appear from the description given below.

In addition, embodiments of the present invention relate to computer readable media or computer program products that include program instructions and/or data (including data structures) for performing various computer-implemented Operations. Examples of computer-readable media include, but are not limited to, magnetic media such as hard disks, floppy disks, and magnetic tape; optical media such as CD-ROM disks; magneto-optical media; semiconductor memory devices, and hardware devices that are specially configured to store and perform program instructions, such as read-only memory devices (ROM) and random access memory (RAM). The data and program instructions of this invention may also be embodied on a carrier wave or other transport medium. Examples of program instructions include both machine code, such as produced by a compiler, and files containing higher level code that may be executed by the computer using an interpreter.

Figure 6:
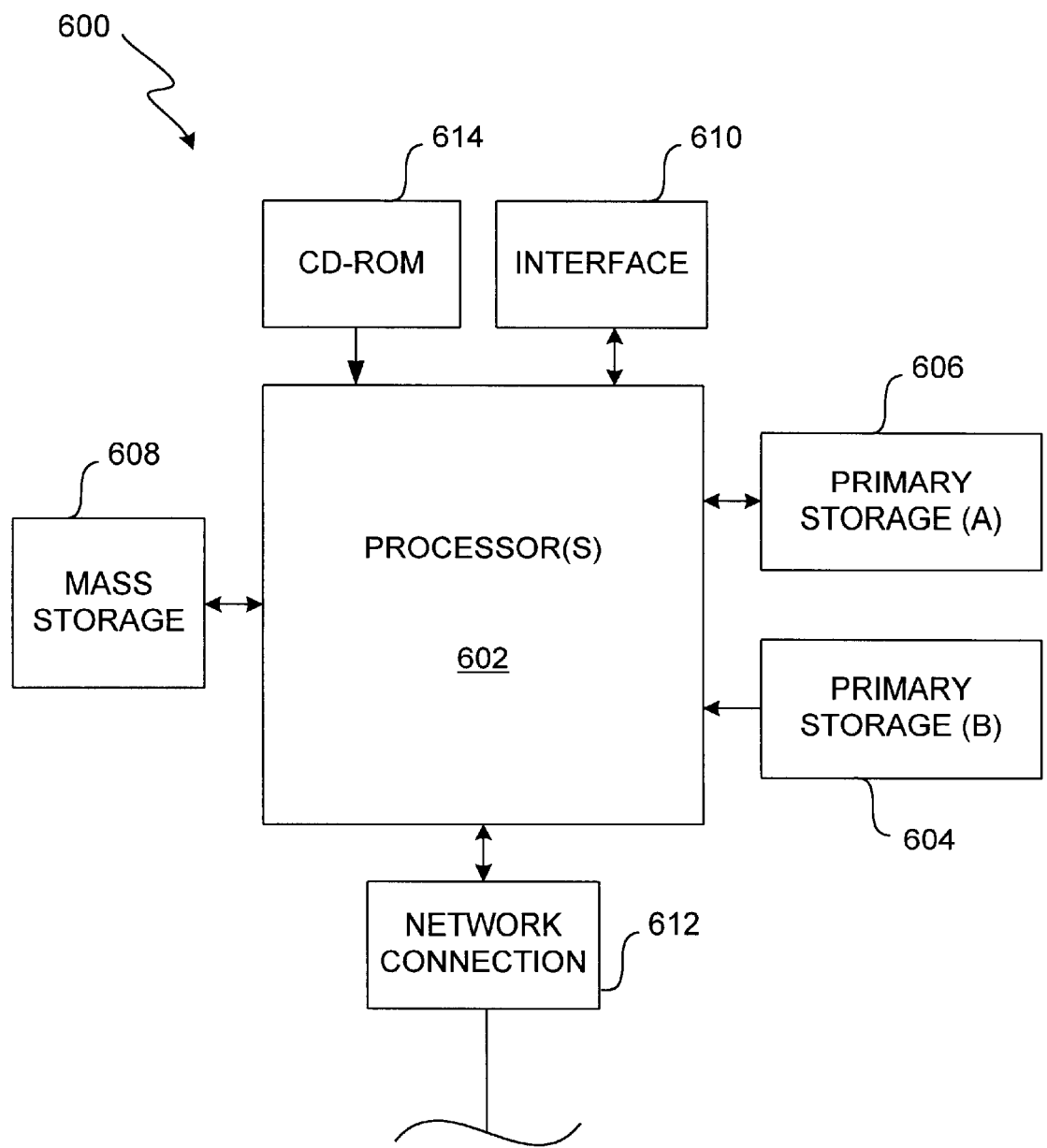
FIG. 6 is a block diagram of a computer system that may be used to implement various aspects of this invention such as the various image analysis algorithms of this invention.

FIG. 6 illustrates a typical computer system that, when appropriately configured or designed, can serve as an experimental control and/or image analysis apparatus of this invention. The computer system 600 includes any number of processors 602 (also referred to as central processing units, or CPUs) that are coupled to storage devices including primary storage 606 (typically a random access memory, or RAM), primary storage 604 (typically a read only memory, or ROM). CPU 602 may be of various types including microcontrollers and microprocessors such as programmable devices (e.g., CPLDs and FPGAs) and unprogrammable devices such as gate array ASICs or general-purpose microprocessors. As is well known in the art, primary storage 604 acts to transfer data and instructions uni-directionally to the CPU and primary storage 606 is used typically to transfer data and instructions in a bi-directional manner. Both of these primary storage devices may include any suitable computer-readable media such as those described above. A mass storage device 608 is also coupled bi-directionally to CPU 602 and provides additional data storage capacity and may include any of the computer-readable media described above. Mass storage device 608 may be used to store programs, data and the like and is typically a secondary storage medium such as a hard disk. It will be appreciated that the information retained within the mass storage device 608, may, in appropriate cases, be incorporated in standard fashion as part of primary storage 606 as virtual memory. A specific mass storage device such as a CD-ROM 614 may also pass data uni-directionally to the CPU.

CPU 602 is also coupled to an interface 610 that connects to one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 602 optionally may be coupled to an external device such as a database or a computer or telecommunications network using an external connection as shown generally at 612. With such a connection, it is contemplated that the CPU might receive information from the network, or might output information to the network in the course of performing the method stops described herein.

In one embodiment, the computer system 600 is directly coupled to (or forms part of) an image acquisition system such as an optical imaging system that captures images of cells. Digital images from the image generating system are provided via interface 612 for image analysis by system 600. Alternatively, the images processed by system 600 are provided from an image storage source such as a database or other repository of cell images. Again, the images are provided via interface 612. Once in the image analysis apparatus 600, a memory device such as primary storage 606 or mass storage 608 buffers or stores, at least temporarily, digital images of the cell. Typically, the cell images will show locations where certain cell markers exist within the cells. In these images, local values of an image parameter (e.g., radiation intensity) associated with a cell marker correspond to amounts or levels of the marker at the locations within the cell shown on the image. With this data, the image analysis apparatus 600 can perform various image analysis operations such as extracting relevant parameters from the cell images, generating the quantitative phenotypes from the relevant parameters, comparing quantitative phenotypes with standards and with quantitative phenotypes from other cell types employed in the studies, and storing the phenotypic information in a database. To this end, the processor may perform various operations on the stored digital image.

Figure 7:
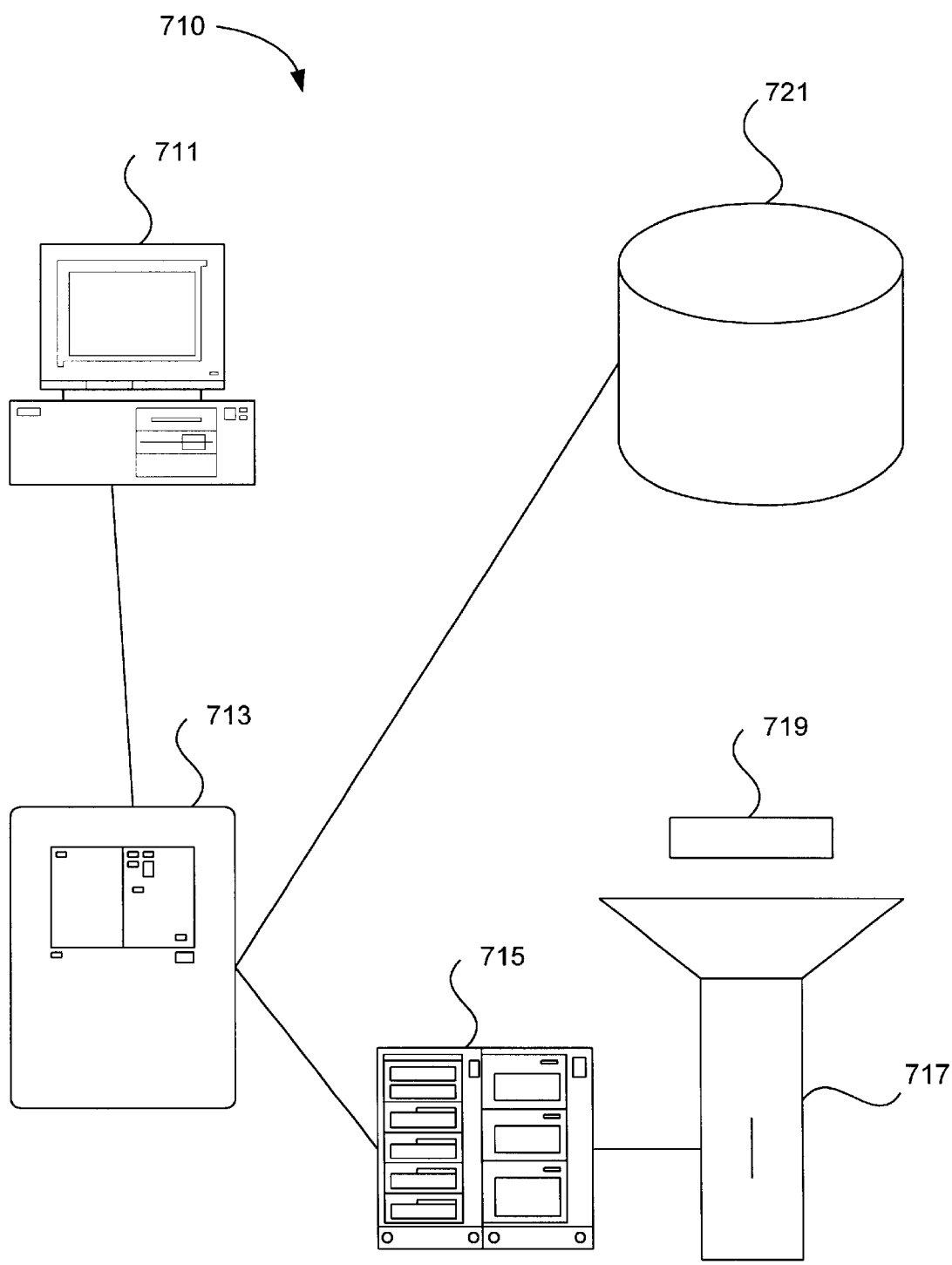
FIG. 7 is a simplified diagram of a complete system for evaluating a biological condition according to an embodiment of the present invention.

FIG. 7 is a simplified diagram of a complete system 710 for evaluating a biological condition according to an embodiment of the present invention. This diagram is merely an example and should not limit the scope of the claims herein. The system 710 includes a variety of elements including a computing device 713, which is coupled to an image processor 715 and is coupled to a database 721. The image processor receives information from an image capturing device 717, which image processor and image capturing device are collectively referred to as the imaging system herein. Suitable imaging systems are discussed in PCT PCT/US00/13154, filed May 12, 2000 in the name of Sabry et al., incorporated herein by reference. See also, U.S. patent application Ser. No. 09/729,7547 filed on Dec. 4, 2000 in the name of Vaisberg and Coleman, which is incorporated herein by reference. The image-capturing device obtains information from a plate 719, which includes a plurality of sites for cells. These cells can be biological cells that are living, fixed, dead, cell fractions, cells in a tissue, and the like. The computing device retrieves the information, which has been digitized, from the image processing device and stores such information into the database. A user interface device 711, which can be a personal computer, a work station, a network computer, a personal digital assistant, or the like, is coupled to the computing device.

Although the above has generally described the present invention according to specific processes and apparatus, the present invention has a much broader range of applicability. In particular, the present invention is not limited to a particular kind of data about a particular cell, but can be applied to virtually any cellular data where an understanding about the workings of the cell is desired. Thus, in some embodiments, the techniques of the present invention could provide information about many different types or groups of cells, substances, and genetic processes of all kinds. Of course, one of ordinary skill in the art would recognize other variations, modifications, and alternatives.

What is claimed is:

1. A method of evaluating the effect of interactions between distinct cell types, the method comprising:
   (a) providing a first cell culture of a first cell type and a second cell culture of a second, different cell type in a microenvironment in which the cells of the first and second cell cultures share a common medium, and wherein the first and second cell types interact in the common medium;
   (b) imaging the first and second cell types after exposure to an agent or stimulus;
   (c) quantitatively evaluating one or more images obtained in (b) to generate quantitative phenotypic representations of the cells; and
   (d) identifying any effects of the agent on the cells in the first and second cell cultures by comparing said quantitative phenotypic representations generated in (c) with phenotypic representations of one or more reference cells, which effects are mediated by interactions between the first and second cell cultures,
   wherein the first cell type is a cancerous epithelial cell type and the second cell type is a mesenchymal cell type, and wherein the first and second cell types are from the same tissue or organ.

2. A method of evaluating the effect of interactions between distinct cell types, the method comprising:
   (a) providing a first cell culture of a first cell type and a second cell culture of a second, different cell type in a microenvironment in which the cells of the first and second cell cultures share a common medium, and wherein the first and second cell types interact in the common medium;
   (b) imaging the first and second cell types after exposure to an agent or stimulus;
   (c) quantitatively evaluating one or more images obtained in (b) to generate quantitative phenotypic representations of the cells; and
   (d) identifying any effects of the agent on the cells in the first and second cell cultures by comparing said quantitative phenotypic representations generated in (c) with phenotypic representations of one or more reference cells, which effects are mediated by interactions between the first and second cell cultures, wherein the first cell type is a cancerous cell type and the second cell type is an immune system cell type.

3. A method of evaluating the effect of interactions between distinct cell types, the method comprising:
   (a) providing a first cell culture of a first cell type and a second cell culture of a second, different cell type in a microenvironment in which the cells of the first and second cell cultures share a common medium, and wherein the first and second cell types interact in the common medium;
   (b) imaging the first and second cell types after exposure to an agent or stimulus;
   (c) quantitatively evaluating one or more images obtained in (b) to generate quantitative phenotypic representations of the cells; and
   (d) identifying any effects of the agent on the cells in the first and second cell cultures by comparing said quantitative phenotypic representations generated in (c) with phenotypic representations of one or more reference cells, which effects are mediated by interactions between the first and second cell cultures, wherein identifying any effects of the agents comprises determining a cell killing potency of the agent.

4. The method of claim 1, 2, or 3, wherein quantitatively evaluating one or more images identifies at least one of a change in migration pattern, growth rate, endocytosis, cell shape, and extracellular matrix deposition of the cells of at least one of the first and second cell cultures.

5. The method of claim 1, 2, or 3, wherein the agent is a chemical compound.

6. The method of claim 1, 2, or 3, wherein the agent is a drug candidate.

7. The method of claim 1, 2, or 3, wherein the biological condition is a disease.

8. The method of claim 7, wherein the biological condition is a cancer.

9. The method of claim 1, 2, or 3, wherein the biological condition is a cancer,
   wherein the first cell type is a cancerous epithelial cell type and the second cell type is an endothelial cell type, and
   wherein the first and second cell types are from the same tissue or organ.

10. The method of claim 1, wherein the agent is predicted to be effective against cancer when the one or more images show that it has an EC50 for the cancerous epithelial cells that is substantially greater than the EC50 for the mesenchymal cells.

11. The method of claim 1, 2, or 3, wherein the common medium is a cell growth medium or a cell support medium.

12. The method of claim 1, 2, or 3, further comprising:
    prior to imaging, allowing the cells of the first and second cell types to grow in the common growth medium.

13. The method of claim 1, 2, or 3, wherein the microenvironment comprises:
    a first compartment in which the first cell culture is grown, and
    a second compartment in which the second cell culture is grown, and
    wherein the common medium contacts the first and second compartments and the first and second cell cultures.

14. The method of claim 13, wherein the first compartment is a base compartment holding the first cell culture at first level,
    wherein the second compartment is provided as an insert to the base compartment, and
    wherein the second compartment holds the second cell culture at a second level, that is above the first level.

15. The method of claim 1, 2, or 3, wherein at least one of the first and second cell types provided in (a) exhibit a biological condition that exists prior to exposure to an agent or stimulus.

* * * * *